United States Patent
Edic et al.

(10) Patent No.: US 6,175,609 B1
(45) Date of Patent: Jan. 16, 2001

(54) METHODS AND APPARATUS FOR SCANNING AN OBJECT IN A COMPUTED TOMOGRAPHY SYSTEM

(75) Inventors: Peter Michael Edic, Albany; Armin Horst Pfoh, Niskayuna, both of NY (US)

(73) Assignee: General Electric Company, Schenectady, NY (US)

(*) Notice: Under 35 U.S.C. 154(b), the term of this patent shall be extended for 0 days.

(21) Appl. No.: 09/295,481

(22) Filed: Apr. 20, 1999

(51) Int. Cl.[7] ..................................... A61B 6/03
(52) U.S. Cl. ............................... 378/7; 378/155
(58) Field of Search .................... 378/4, 7, 147, 378/155, 901

(56) References Cited

U.S. PATENT DOCUMENTS

| | | | |
|---|---|---|---|
| 4,101,768 | * 7/1978 | Lill | 378/7 |
| 4,707,608 | * 11/1987 | DiBianca | 250/389 |
| 5,144,141 | 9/1992 | Rougeot et al. | 250/369 |
| 5,231,654 | 7/1993 | Kwasnick et al. | 378/147 |
| 5,231,655 | 7/1993 | Wei et al. | 378/147 |
| 5,293,417 | 3/1994 | Wei et al. | 378/147 |
| 5,303,282 | 4/1994 | Kwasnick et al. | 378/147 |
| 5,430,298 | 7/1995 | Possin et al. | 250/370.11 |

* cited by examiner

Primary Examiner—David V. Bruce
(74) Attorney, Agent, or Firm—Donald S. Ingraham; Douglas E. Stoner

(57) ABSTRACT

The present invention, in one form, is a system for reducing contribution of scatter signal to an image of an object constructed from projection data acquired during a computed tomography scan. The system includes an x-ray source which emits an x-ray beam toward a detector array. A collimator plate is movable with respect to the detector array. The system is configured to move the collimator between a first position and a second position. In the first and second positions, the collimator does not cover the detector array, i.e., the collimator does not collimate the x-ray beam impacting the detector array. When moving between the first and second positions, the collimator at least partially covers the detector array, i.e., the collimator at least partially collimates the x-ray beam impacting the detector array. A first signal intensity at the detector array is obtained when the collimator is in the first position and a second signal intensity at the detector array is obtained when the collimator is moved between the first and second position. The determined signal intensities are then utilized to determine the scatter signal of the x-ray beam and to generate substantially uncorrupted projection data.

18 Claims, 4 Drawing Sheets

METHODS AND APPARATUS FOR SCANNING AN OBJECT IN A COMPUTED TOMOGRAPHY SYSTEM

BACKGROUND OF THE INVENTION

This invention was made with Government support under Government Contract No. 70NANB5H1148 awarded by NIST. The Government has certain rights in this invention.

This invention relates generally to computed tomography (CT) imaging and, more particularly, to scanning an object of interest with a CT scanner.

In at least one CT system configuration, and during a scanning process, an x-ray source projects an x-ray beam towards a detector and the x-ray beam passes through the object being imaged. In known industrial CT systems, for example, the object being imaged is positioned on a manipulator which rotates the object during the scanning process. The beam, after being attenuated by the object, impinges upon the detector. The detector includes an array of generally rectangular detector cells, and the intensity of the attenuated beam radiation received at each detector cell is dependent upon the attenuation of the x-ray beam by the object. Each detector cell, or element, of the array produces a separate electrical signal that is a measurement of the beam intensity at the detector cell location. The attenuation measurements from all the detector cells are acquired separately to produce a transmission profile.

The x-ray beam received at the detector array typically includes two components, namely, a primary signal and a scatter signal. The scatter signal typically reduces resolution and contrast in reconstructed images, which is undesirable. To reduce the impact of scatter signals, a collimator can be placed over the detector. The collimator is configured to substantially prevent scatter beams from impinging upon the detector cells.

While stationary collimators generally are satisfactory for reducing the affects of scatter signals in one-dimensional, or linear, detector arrays, such collimators may not provide optimum results when used in connection with multi-dimensional, or area, detector arrays. Particularly, the pitch of the detector elements in area arrays may be orders of magnitude less than the pitch of the detector elements in linear arrays, and stationary collimators may not be as effective when used in connection with such small pitch detector elements.

To reduce the contribution of the scatter signal received at area detector arrays, a CT system can be configured to directly measure either the scatter signal or the primary signal. The component of the measured signal due to scatter can be determined and then subtracted from the total signal to generate substantially uncorrupted projection data. Directly measuring either the scatter signal or the primary signal, however, is complex and time consuming.

It would be desirable to reduce the contribution of scatter to an image reconstructed from data collected by an area detector in a CT system. It also would be desirable to reduce the contribution of scatter without directly measuring the primary or scatter signal.

SUMMARY OF THE INVENTION

A computed tomography system, in one embodiment, includes a movable collimator and the system is adapted to implement a scatter correction algorithm to estimate a primary signal and a scatter signal without requiring direct measurement of such signals. During a scan, the collimator is moved from a first position to a second position. When the collimator is in the first or second position, the collimator is not located over the detector and does not collimate the beam impinging upon the detector. As the collimator moves between the first and second positions, however, the collimator at least partially collimates the x-ray beam impinging upon the detector array. A first signal intensity at the detector array is obtained when the collimator is in the first or second position, and a second signal intensity at the detector array is obtained after the collimator is moved between the first and second positions. These signal intensities are then utilized to estimate the scatter signal. The estimated scatter signal is then used to generate substantially uncorrupted projection data.

DETAILED DESCRIPTION

Figure 1:
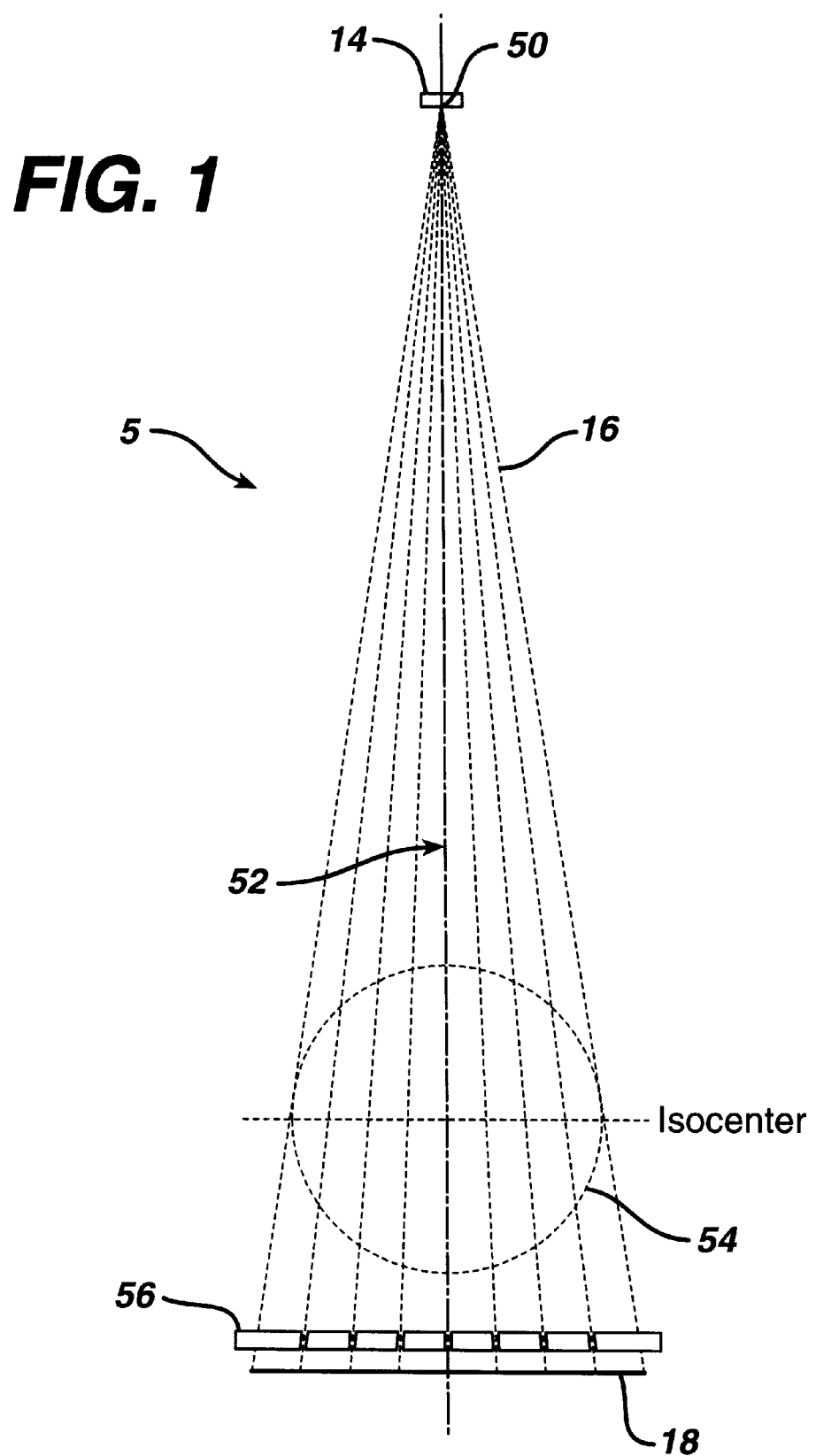
FIG. 1 is a schematic view of the CT imaging system with a stationary collimator.

Referring to FIG. 1, and with respect to operation of an x-ray source 14 in a CT system 5, an x-ray beam 16 emanates from a focal spot 50 of source 14. X-ray beam 16 is projected along a fan beam axis 52 centered within fan beam 16 and through an object bounded by workpiece bounding circle 54. X-ray beam 16 is attenuated by the object and then is collimated by a stationary collimator 56 so that it is positioned over detector array 18. Collimated beam 16 is projected toward detector array 18 which, as described above, produces electrical signals that are representative of the intensity of an impinging x-ray beam at various locations on detector array 18.

Figure 2A:
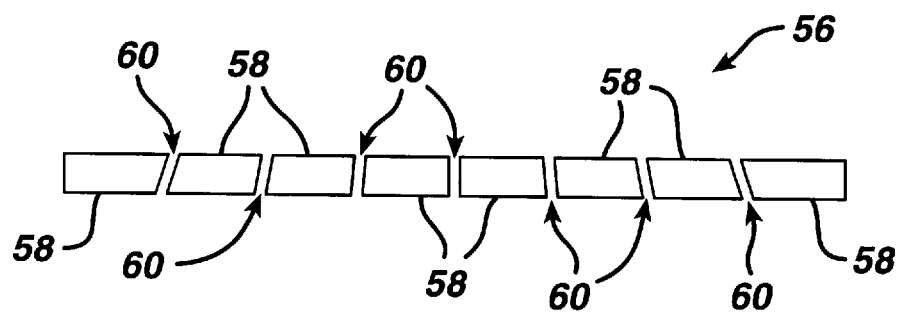
FIG. 2A is a top view illustration of the collimator shown FIG. 1.
Figure 2B:
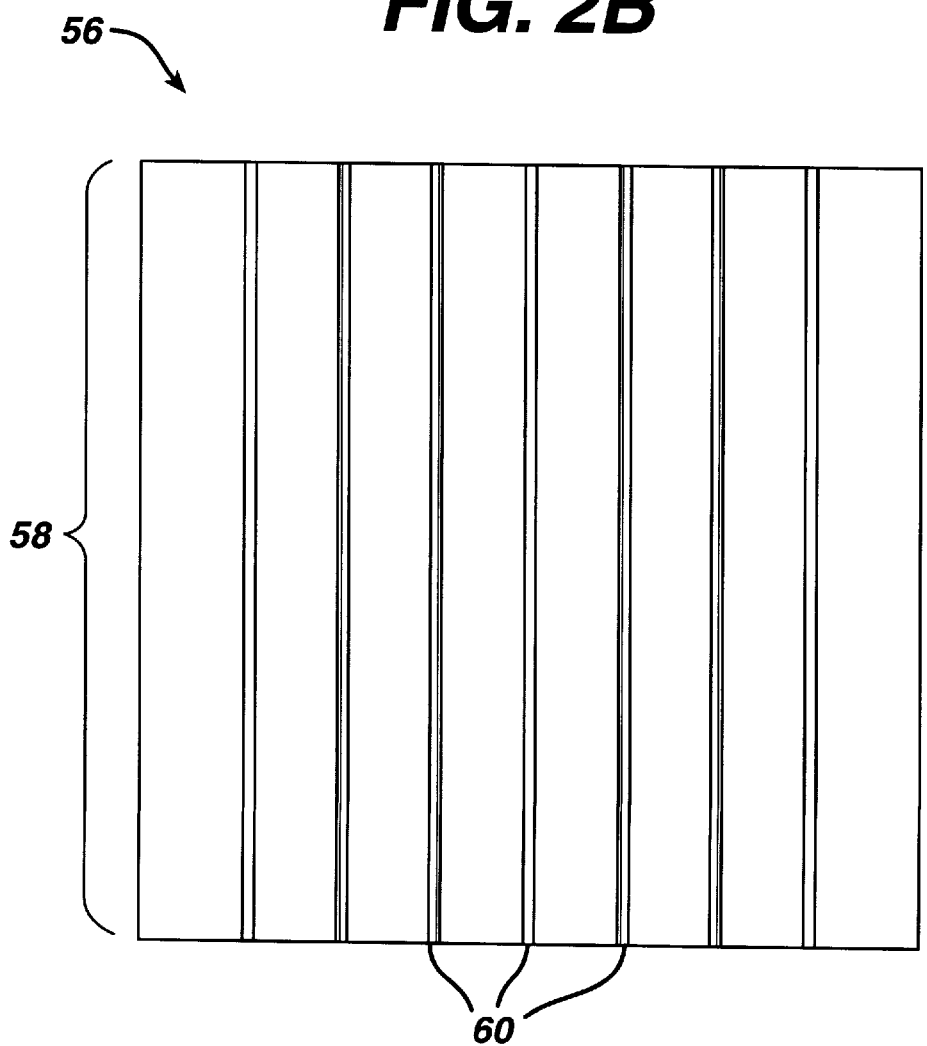
FIG. 2B is a front view illustration of the collimator shown in FIG. 1.

Referring now to FIGS. 2A and 2B, collimator 56 includes a substantially square collimator plate 58 fabricated from x-ray attenuating material and having a plurality of slits, or openings, 60 therein. Collimator plate 58 typically has dimensions that correspond to the active area of detector array 18 (FIG. 1) and slits 60 are focally aligned with x-ray source 14. Collimator plates that have dimensions less than those of the active array (especially dimensions along an axis perpendicular to the axis of movement 130 of the collimator) are less effective in blocking scatter signal incident on the detector array.

Collimator 56 prevents scatter signals propagating along an angular path not parallel to slits 60 from interacting with detector array 18. The x-ray attenuating material of collimator 56 covers several detector elements (pixels), and slits 60 collimate signals for a few detector columns (rows). By blocking such signals from detector array 18, image quality is believed to be improved because erroneous data which result from such scatter signals are not generated.

Figure 3:
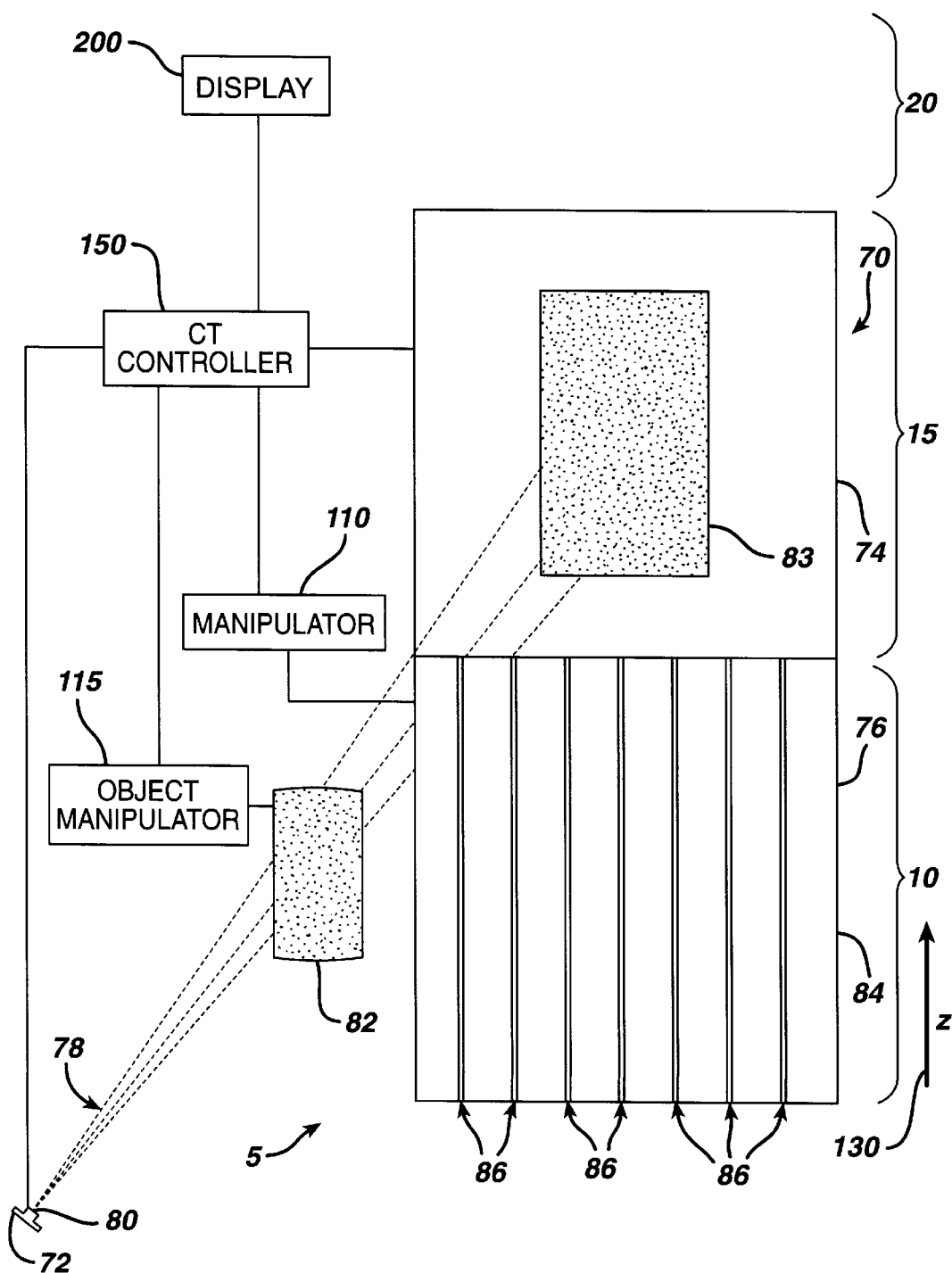
FIG. 3 is a schematic view of a CT imaging system including a movable collimator in accordance with one embodiment of the present invention.

FIG. 3 is a schematic view of a CT imaging system 70 including an x-ray source 72, an area detector array 74, and a CT controller 150. Controller 150 is coupled to x-ray source 72, detector 74 and a collimator manipulator 110, which in turn is coupled to a movable collimator 76. Controller 150 is configured to control components of the CT system and to process signals from detector 74 so as to generate signals for a display 200 of images of the object 82 to be imaged. As used herein, "adapted to," "configured to," and the like refer to components that comprise or are coupled to control devices such as programmable computer devices, application specific integrated circuits, or the like to execute a program or motion in accordance with a selected control algorithm.

In typical operation, x-ray source 72 projects a cone beam of x-rays 78 from a focal spot 80 and toward detector array 74. Detector array 74 is formed by detector elements (not shown in FIG. 3) which together sense the x-rays that pass through and around an object of interest, or workpiece, 82. A shaded area 83 on array 74 illustrates a location at which projected x-rays passing directly from source 72 through the workpiece 82 towards detector 74 are incident on detector array 74 (for the particular arrangement shown in FIG. 3). Each detector element produces an electrical signal that represents the intensity of the incident x-ray beam. During a scan, object 82 is typically rotated by an object manipulator 115 so that a plurality of radiographic views of object 82 can be obtained. The signals from detector 74 for this plurality of views of object 82 are generated and processed by controller 150. The arrangement illustrated, in which object 82 is manipulated to obtain a desired plurality of radiographic images, is commonly used in industrial CT systems; alternatively, the radiation source and detector, in fixed relation to one another, can be rotated about the object to be imaged to obtain the desired radiographic data sets, as is commonly done in medical systems.

Collimator 76 is configured to move relative to detector array 74 and includes a collimator plate 84 fabricated from x-ray attenuating material and having a plurality of slits, or openings, 86 therein. Collimator plate 84 is sized so that when it is positioned and centered over array 74, it substantially extends across entire detector array 74. Collimator plate 84 is aligned along a respective collimator plate axis 130 (illustrated by the arrow in FIG. 3) with respect to array 74 so that slits 60 are focally aligned with x-ray source 72. By way of example and not limitation, slits 86 in collimator plate 84 extend along the collimator plate axis 130 (shown in the figure as the z-axis). Collimator plate 84 is movable in the z-direction between first and second positions. Collimator manipulator 110 is configured (for example, with electromechanical devices such as motors coupled to drive the collimator plate along tracks aligned with collimator plate axis 130) between a first position 10, a plurality of intermediate positions 15 (illustrated in FIG. 3 as a region in which the collimator plate 84 at least partially overlies the detector array 74), and a second position 20. In first position 10 and second position 20, collimator 76 is disposed such that radiation passing directly from source 72 towards array 74 is not incident on the collimator plate. In any of a plurality of intermediate positions 15, the collimator plate is disposed in a spatial relation with respect to source 72 and detector 74 such that radiation passing directly from source 72 towards detector 74 is incident on at least a portion of collimator plate 84. As collimator 76 moves between the first and second positions, collimator 76 at least partially covers detector array 74.

During a scan, CT controller 150 controls apparatus to generate at least two exposures of the object 82. The period of each of the two exposures is the same. In the first exposure, object 82 is imaged so that the exposure first signal intensity at detector array 74 is obtained when collimator 76 is in a position (e.g., first position 10, or alternatively, second position 20) in which the collimator does not overlie the detector ("overlie", as used herein, refers to the collimator being disposed at least partially in a direct line between radiation source 72 and detector array 74). A second exposure is obtained as collimator plate 84 is moved between first position 10 and second position 20 (or alternatively, between second position 20 and first position 10). The second exposure signal thus represents the detected radiation passing through the collimator while the collimator passes through the plurality of intermediate positions 15 in which the collimator overlies at least a portion of the detector. Data from the two exposures are then utilized to determine the scatter signal of x-ray beam 78 and to generate substantially uncorrupted projection data as described below.

By way of example and not limitation, collimator 76 initially is positioned below detector array 74, i.e., in the first position 10, so that detector array 74 receives uncollimated x-rays 78. During a scan, the manipulator moves collimator 76 along the collimator axis 130 (as shown in FIG. 3, vertically, i.e., in the z-direction), over detector array 74 through the plurality of intermediate position 15 in which the collimator overlies the array so that detector array 74 receives collimated x-rays 78. Collimator 76 is moved along the collimator axis until it is completely above detector array 74, i.e., in the second position 20, so that detector array 74 again receives uncollimated x-rays 78. The time interval during which collimator 76 moves between the first position and the second position corresponds to one exposure interval, e.g., the time required to irradiate object 82 to obtain data sufficient for one view of object 82.

Collimator 76 remains above detector array 74, e.g., in the second position, until projection data from N−1 views have been acquired, where N is a number of views between temporal primary signal samplings. For example, the primary signal may be sampled every 20 views, e.g., N=20. During the next exposure interval, the manipulator moves collimator 76 downward, past detector array 74, until collimator 76 is positioned in the first position. Collimator 76 remains in the first position and data is obtained for another N−1 views, and then is moved again to the second position. The manipulator oscillates collimator 76 between the first position and the second position, as described above, for an entire scanning period. The number of views N may be pre-selected and stored, for example, in a CT system computer.

During the scan, a first signal intensity $I_1(y,z)$ is determined for each location (y,z) in detector array 74 when collimator 76 does not cover such location (y,z), e.g., when the collimator is in the first and second positions, and a second signal intensity $I_2(y,z)$ is determined for the location (y,z) when collimator 76 is in transit through the plurality of intermediate positions so that during the exposure period to determine the second signal intensity the collimator at least partially covers such location (y,z). Particularly, when collimator 76 is in either the first position or the second position, a first data set that is representative of first signal intensity $I_1(y,z)$ is collected and stored. As collimator 76 is moved between the first and second positions, a second data set that is representative of second signal intensity $I_2(y,z)$ is collected and stored. The data sets are then used to determine the primary signal and scatter signal component of x-rays 78 received at detector array 74.

Particularly, first signal intensity $I_1(y,z)$ is described as:

$$I_1(y,z)=p(y,z)+s(y,z) \qquad (1)$$

where:

p(y,z) is a measured primary signal intensity in detector array 74;

s(y,z) is a measured scatter signal intensity in detector array 74;

y is a horizontal dimension of detector array 74; and z is a vertical dimension of detector array 74.

Second signal intensity $I_2(y,z)$, however, does not include a significant scatter signal s(y,z) because collimator 76 reduces the scatter signal s(y,z) incident upon detector array 74 when collimator 76 is moved between the first and second positions. The amount of the reduction is a function of the collimator plate size in comparison with the array size. For example, if the collimator plate dimensions substantially correspond to the dimensions of the array, the scatter signal reduction is about 50%; if the collimator plate dimension are less than that of the array (e.g., the dimension of the collimator plate perpendicular to the axis of movement of the collimator plate), then the reduction in the scatter signal is less than 50%. Accordingly, second signal intensity $I_2(y,z)$ may be described as:

$$I_2(y,z) = p(y,z) + \alpha s(y,z) \qquad (2)$$

where $\alpha$ is a fraction.

Solving using both first signal intensity $I_1(y,z)$ and second signal intensity $I_2(y,z)$, primary signal p(y,z) and scatter signal s(y,z) at each location (y,z) on detector array 74 can be represented in the slit regions as follows:

$$p(y, z) = \frac{I_2(y, z) - \alpha I_1(y, z)}{1 - \alpha} \qquad (3)$$

and $$s(y, z) = \frac{I_1(y, z) - I_2(y, z)}{1 - \alpha} \qquad (4)$$

The above equations are valid at least with respect to portions of detector array 74 aligned with slits 86, neglecting vertical in-plane scatter. The proportion of the scatter signal that is measured is a function of the height of collimator 76. The determined primary and scatter signals p(y,z) and s(y,z), respectively, are then utilized to generate projection data. More particularly, after determining scatter signal s(y,z) received at detector array 74, a squared-error between a polynomial and the scatter samples is minimized across several rows of detector array 74 to generate a 2-D map of the scatter. The scatter signal is thus approximated by a polynomial surface that minimizes the squared error between the samples and the polynomial.

The scatter signal can be determined at locations (y,z) in the slit regions of the detector. Since the slit regions are located in positions that span the width of the detector array (e.g., the width of the detector is aligned along the horizontal axis as illustrated in FIG. 3), the scatter signal is sampled in that direction. This sampling technique is suitable since the scatter signal contains low frequency signal content; thus, according to the Nyquist theorem, pertinent data about the scatter signal is obtained from this sampling technique. Using the scatter signal sampled at various locations across the imager, a 2D surface is fit to the samples using a least-squares approximation method. This surface is then used to approximate the scatter signal at each (y,z) location in the detector. For subsequent data acquisitions, the approximated scatter signal (e.g., a scatter signal interpolated from temporally adjacent samples of scatter) will be subtracted from the measured intensity signal to generate a scatter free signal which will be used for image reconstruction and display (e.g., with a video or print out display means 200).

The above-described CT system 70 and scatter correction algorithm are believed to improve image quality by reducing scatter error. In addition, such system and algorithm reduce the contribution of the scatter signal received at area detector array 74 without requiring direct measurement of the scatter and primary signals.

Figure 4:
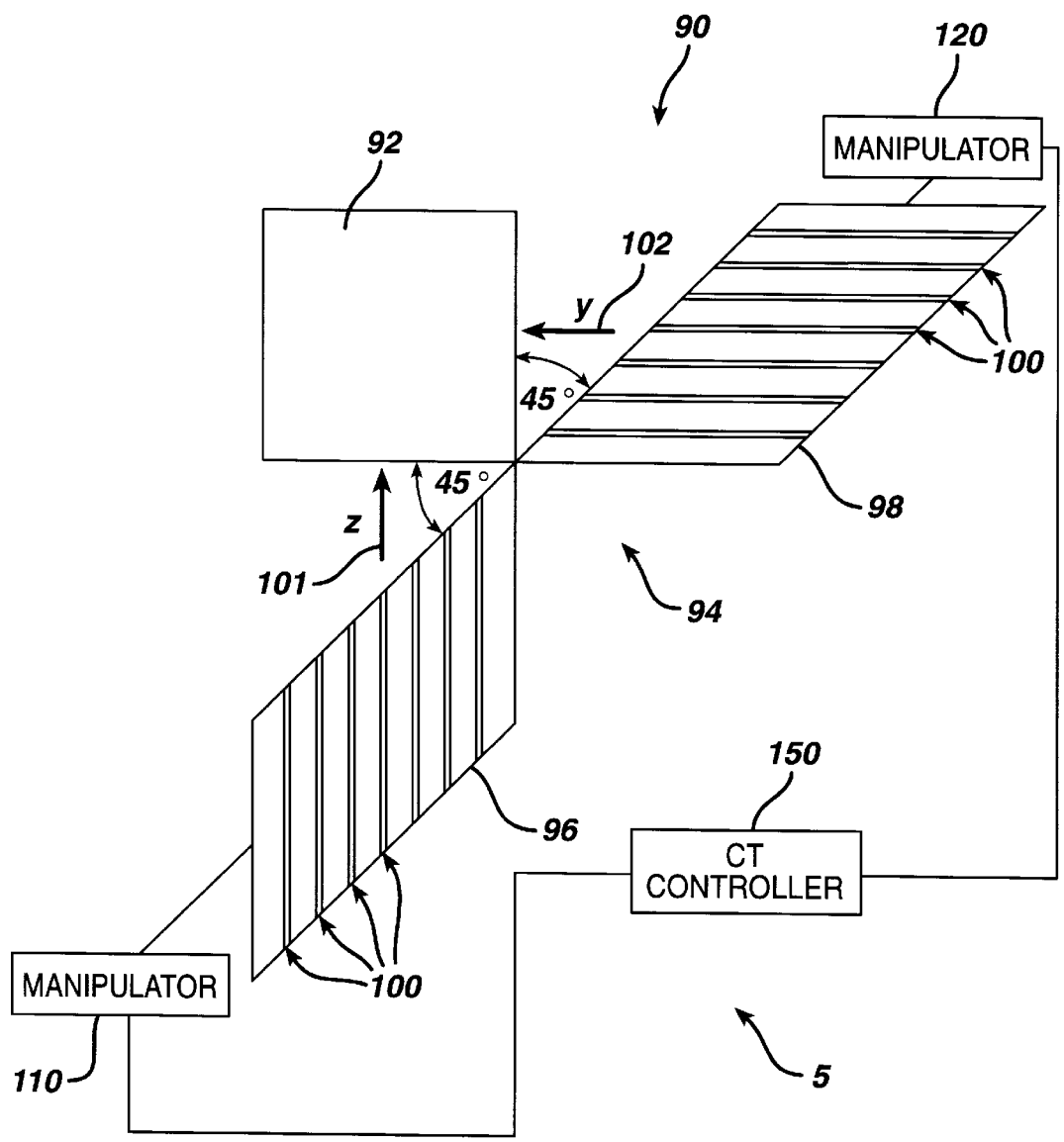
FIG. 4 is a partial schematic view of a CT imaging system including a movable post-patient collimator in accordance with another embodiment of the present invention.

To reduce the effect of any in-plane scatter signals penetrating collimator slits 86, an alternative arrangement of collimator 76 is used. For example, FIG. 4 is a partial schematic view of a CT imaging system 90 including an area detector array 92 and a movable collimator 94 in accordance with another embodiment of the present invention. Detector array 92 is formed by detector elements (not shown in FIG. 4) which together sense the projected x-rays that pass through an object of interest, or workpiece. Each detector element produces an electrical signal that represents the intensity of an incident x-ray beam and hence the attenuation of the beam as it passes through the object.

Collimator 94 comprises a first collimator plate 96 and a second collimator plate 98, each of which is configured to move relative to detector array 92. Each plate 96 and 98 is fabricated from x-ray attenuating material and includes a plurality of slits, or openings, 100 therein. Collimator plates 96 and 98, respectively, typically are sized to substantially extend across entire detector array 92 (e.g., have dimensions that correspond with the active area of array 92) and slits 100 are focally aligned with an x-ray source. In addition, collimator plates 96 and 98 each are configured to substantially ensure that each pixel where a primary signal is to be measured has the same proportion of scatter signal.

First collimator plate 96 is movable in the z-direction along first collimator axis 101 and second collimator plate 98 is movable in the y-direction along second collimator axis 102. Particularly, collimator plate 96 is coupled to a first collimator manipulator 110, which is configured to move collimator plate 96 relative to detector array 92 and which also is configured to received signals from a CT control mechanism 150. Similarly, collimator plate 98 is coupled to a second collimator manipulator, which is configured to move collimator plate 98 relative to detector array 92 and which also is configured to received signals from a CT control mechanism. Collimator plate 96 is movable in the z-direction between a first and a second position (as that term is used above with respect to the arrangement illustrated in FIG. 3). In the first and second positions, collimator plate 96 does not overlie detector array 92, i.e., collimator plate 96 is not positioned between the x-ray source and detector array 92. As first collimator plate 96 is moved between its respective first and second positions, collimator plate 96 at least partially covers detector array 92, i.e., where collimator plate 96 is positioned at least partially between the x-ray source and detector array 92. Similarly, second collimator plate 98 is movable in the y-direction between respective second collimator plate first and second positions, in which second collimator plate 98 does not overlie detector array 92. As second collimator plate 98 is moved between its respective first and second positions, collimator plate 98 at least partially overlies detector array 92.

During a scan, collimator plates 96 and 98 are synchronously moved along their respective axes with respect to detector array 92, as described above with respect to collimator plate 76 and detector array 74. "Synchronously moved" means that the movement of first and second collimator plates is coordinated so that each plate respectively begins to cover pixels in array 92 at the same time and is moved clear of pixels in array 92 at the same time. Specifically, the first manipulator moves first collimator plate 96 in the z-direction between its respective first position and second position so that during an exposure interval first collimator plate 96 is located in a plurality of intermediate positions (between the first and second positions) in which the first collimator plate 96 at least partially collimates x-rays incident on detector array 92. Similarly, second manipulator 120 moves second collimator plate 98 in the y-direction between its respective first and second positions so that during an exposure interval second collimator plate 98 is located where it also at least partially collimates x-rays incident on detector array 92. The time interval during which collimator plates 96 and 98 move between their respective first positions and second positions typically is one exposure interval, e.g., the time required to obtain one view of an object of interest.

First and second signal intensities $I_1(y,z)$ and $I_2(y,z)$ are then determined in accordance with the above-described equations. Signal intensities $I_1(y,z)$ and $I_2(y,z)$ are utilized to determine scatter signal $s(y,z)$ at each location $(y,z)$ in detector array 92, as described above, and to generate substantially uncorrupted projection data. CT system 90 is believed to substantially reduce the impact of in-plane scatter signals.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, many other CT systems may be used. Accordingly, the spirit and scope of the invention are to be limited only by the terms of the appended claims.

What is claimed is:

1. A method for generating projection data of an object 83 scanned by a computed tomography (CT) system, the computed tomography system including an x-ray source for projecting an x-ray beam toward a detector array and at least one collimator 84, said method comprising the steps of:
   moving the at least one collimator plate 86 from a first position 10 to a second position;
   determining a first signal intensity representative of the intensity of the x-ray beam received at the detector array when said at least one collimator is in the first position;
   determining a second signal intensity representative of the intensity of the x-ray beam received at the detector array when said at least one collimator at least partially overlies said detector array as said collimator is moved between said first position and said second position; and
   generating projection data utilizing the first and second signal intensities.

2. A method in accordance with claim 1 wherein each of said first and second positions of a first collimator plate are aligned along a first collimator axis with respect to the detector array.

3. A method in accordance with claim 2 wherein the CT system comprises two collimator plates and each of the respective first and second positions of a second collimator plate are aligned along a second collimator axis with respect to the detector array, the second collimator axis being orthogonal to the first collimator axis.

4. A method in accordance with claim 3 wherein said first and second collimator plates are moved synchronously while determining said second signal intensity.

5. A method in accordance with claim 2 wherein the first signal intensity is determined in accordance with following relationship:

$$I_1(y,z) = p(y,z) + s(y,z)$$

where:
  $I_1(y,z)$ is the first signal intensity in the detector array;
  $p(y,z)$ is a measured primary intensity in the detector array;
  $s(y,z)$ is a measured scatter intensity in the detector array;
  $y$ is a horizontal dimension of the detector array; and
  $z$ is a vertical dimension of the detector array.

6. A method in accordance with claim 5 wherein the second signal intensity is determined in accordance with:

$$I_2(y,z)\ p(y,z) + \alpha s(y,z)$$

where:
  $I_2(y,z)$ is the second signal intensity in the detector array; and
  $\alpha$ is a fraction.

7. A method in accordance with claim 6 wherein generating projection data utilizing the first and second signal intensities comprises the step of determining a scatter signal utilizing the first and second signal intensities.

8. A method in accordance with claim 7 wherein the scatter signal is determined in accordance with the following relationship:

$$s(y, z) = \frac{I_1(y, z) - I_2(y, z)}{1 - \alpha}.$$

9. A system for generating projection data in a computed tomography (CT) system for an object of interest, said system comprising:
   an x-ray source;
   a detector array for receiving x-ray beams projected by said x-ray source;
   at least one movable collimator plate disposable at a plurality of positions between the x-ray source and the detector array;
   a manipulator coupled to the at least one collimator plate for disposing the plate in a selected position along an axis with respect to the detector array;
   a CT controller coupled to said detector array to receive radiation detection signals therefrom, the controller being configured to process said detection signals and generate a scatter correction signal in response to detection signals corresponding to respective positions of the at least one collimator plate.

10. A system in accordance with claim 9 comprising a first collimator plate movable along a first collimator axis with respect to the detector array between a respective first position and a respective second position and intermediate positions therebetween, said first collimator plate being disposed so as to be exposed to incident radiation passing from said source to said detector array when disposed in said intermediate positions.

11. A system in accordance with claim 9 further comprising a second collimator plate movable along a second collimator axis with respect to the detector array, said second collimator axis being orthogonal to said first collimator axis.

12. A system in accordance with claim 11 wherein said CT controller is configured to:

determine a first signal intensity representative of an intensity of said x-ray beam received at said detector array when said at least one collimator plate is in said first position; and determine a second signal intensity representative of an intensity of said x-ray beam received at said detector array when said at least one collimator is disposed in a plurality of intermediate positions between said first and second positions.

13. A system in accordance with claim 12 wherein said CT controller is configured to generate projection data utilizing said first signal intensity and said second signal intensity.

14. A system in accordance with claim 13 wherein said first signal intensity is determined in accordance with the following relationship:

$$I_1(y,z) \, p(y,z)+s(y,z)$$

where:

$I_1(y,z)$ is said first signal intensity in said detector array;

$p(y,z)$ is a measured primary intensity in said detector array;

$s(y,z)$ is a measured scatter intensity in said detector array;

y is a horizontal dimension of said detector array; and z is a vertical dimension of said detector array.

15. A system in accordance with claim 14 wherein said second signal intensity is determined in accordance with the relationship:

$$I_2(y,z)=p(y,z)+\alpha s(y,z)$$

where:

$I_2(y,z)$ is said second signal intensity in said detector array; and $\alpha$ is a fraction.

16. A system in accordance with claim 15 wherein to generate projection data utilizing said first signal intensity and said second signal intensity, said system is configured to determine a scatter signal utilizing said first signal intensity and said second signal intensity.

17. A system in accordance with claim 16 wherein the CT controller is configured to determine said scatter signal in accordance with the following relationship:

$$s(y, z) = \frac{I_1(y, z) - I_2(y, z)}{1 - \alpha}.$$

18. A system in accordance with claim 11 wherein said first collimator plate is coupled to a first collimator manipulator and said second collimator plate is coupled to a second collimator manipulator; each of said first and second collimator plate manipulators being coupled to said CT controller and configured to move said first and second collimator plates synchronously during an exposure period to generate data for said second signal intensity.

* * * * *